United States Patent
Chen et al.

(10) Patent No.: US 10,760,096 B2
(45) Date of Patent: Sep. 1, 2020

(54) HUMAN TYPE 55 REPLICATION DEFECTIVE ADENOVIRUS VECTOR, METHOD FOR PREPARING SAME AND USES THEREOF

(71) Applicant: GUANGZHOU N BIOMED CO., LTD., Guangzhou, Guangdong (CN)

(72) Inventors: Ling Chen, Guangdong (CN); Liqiang Feng, Guangdong (CN)

(73) Assignee: GUANGZHOU N BIOMED CO., LTD., Guangzhou (CN)

( * ) Notice: Subject to any disclaimer, the term of this patent is extended or adjusted under 35 U.S.C. 154(b) by 0 days.

(21) Appl. No.: 15/784,224

(22) Filed: Oct. 16, 2017

(65) Prior Publication Data

US 2018/0179554 A1  Jun. 28, 2018

Related U.S. Application Data

(63) Continuation of application No. PCT/CN2015/095730, filed on Nov. 27, 2015.

(30) Foreign Application Priority Data

Apr. 15, 2015  (CN) .......................... 2015 1 0179459

(51) Int. Cl.

| | |
|---|---|
| *C12N 15/86* | (2006.01) |
| *C12N 15/861* | (2006.01) |
| *A61K 35/761* | (2015.01) |
| *A61K 39/02* | (2006.01) |
| *C12N 15/90* | (2006.01) |
| *A61K 39/00* | (2006.01) |

(52) U.S. Cl.
CPC .......... *C12N 15/86* (2013.01); *A61K 39/0208* (2013.01); *C12N 15/861* (2013.01); *C12N 15/902* (2013.01); *A61K 2039/5256* (2013.01); *C12N 2710/10021* (2013.01); *C12N 2710/10034* (2013.01); *C12N 2710/10062* (2013.01); *C12N 2710/10334* (2013.01); *C12N 2710/10343* (2013.01); *C12N 2710/10351* (2013.01); *C12N 2710/10371* (2013.01); *C12N 2800/22* (2013.01); *C12N 2800/24* (2013.01)

(58) Field of Classification Search
None
See application file for complete search history.

(56) References Cited

U.S. PATENT DOCUMENTS 7,468,181 B2 * 12/2008 Vogels .................. C12N 15/86
424/93.2

OTHER PUBLICATIONS

Zhou et al. An efficient method of directly cloning chimpanzee adenovirus as a vaccine vector. Nov. 2010. Nat Protoc. vol. 5, No. 11, pp. 1775-1785. (Year: 2010).*
Zhang et al. (Genome Sequence of Human Adenovirus Type 55, a Re-Emergent Acute Respiratory Disease Pathogen in China. Nov. 2012. Journal of Virology. vol. 86, No. 22, pp. 12441-12442. (Year: 2012).*
Xingguo Mei, Construction of Adenovirus Carrier, Microcarrier Drug Delivery System, 2009, p. 332.
Liuxin Dong, Expression of Type-specific E1B55K Gene Enhanced the Propagation of Human Adenovirus Type 41 in 293 Cells, China Doctoral Dissertations Full-text Database, 2011, pp. E059-E011.
Chengjun Wu, Construction of Ad35 Adenovirus Carrier and the Research of Viral Albumen Immunogenicity, China Doctoral Dissertations Full-text Database, 2011, pp. E059-E094.
1st Office Action of counterpart Chinese Patent Application No. 201510179459.7 dated Jul. 7, 2017.

* cited by examiner

*Primary Examiner* — Channing S Mahatan

(57) ABSTRACT

Provided are a human type 55 replication defective adenovirus vector, a method for preparing the same and uses thereof. The human type 55 replication defective adenovirus vector is prepared by the following method: knocking out E1 and E3 genes from Ad55, substituting the open reading frame 6 or the open reading frames 2, 3, 4, 6, and 6/7 of E4 gene in Ad55 genome with the corresponding open reading frames of Ad5 genome. In addition, an exogenous gene expression cassette may also be integrated into the E1 gene region of Ad55.

16 Claims, 8 Drawing Sheets

Specification includes a Sequence Listing.

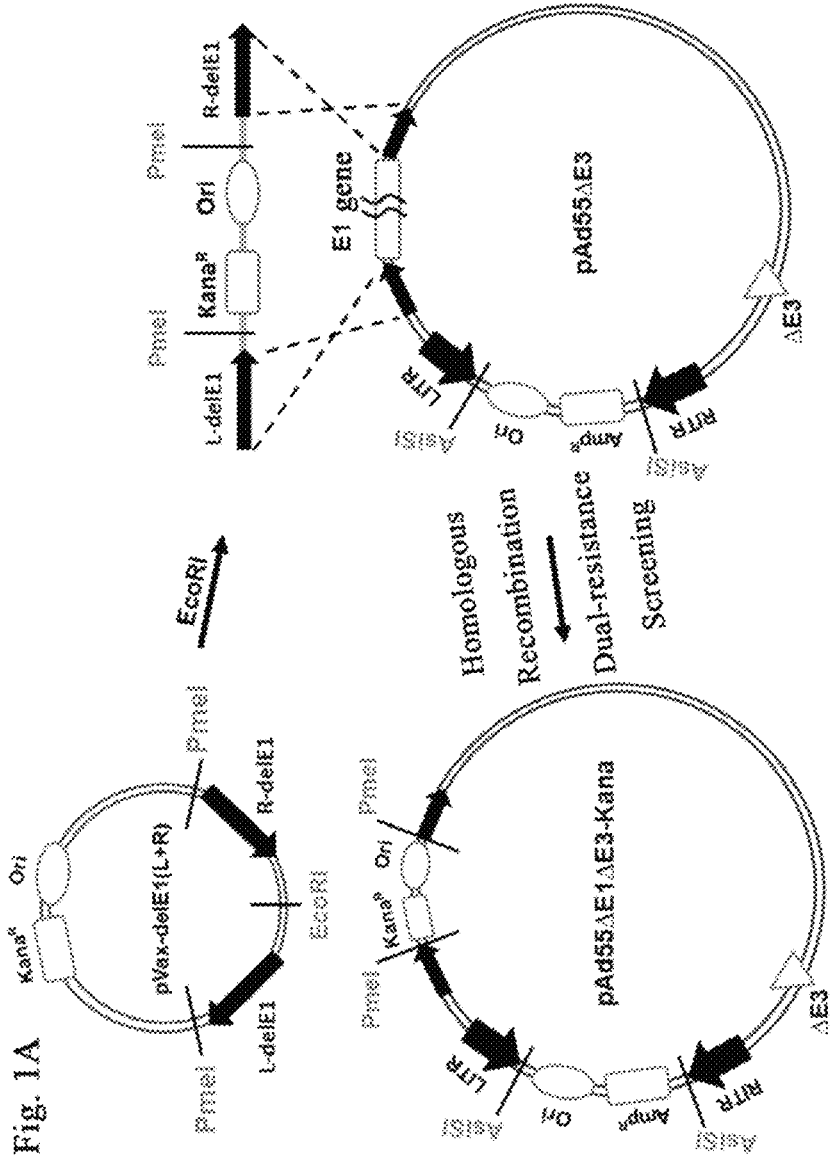
Fig. 1A
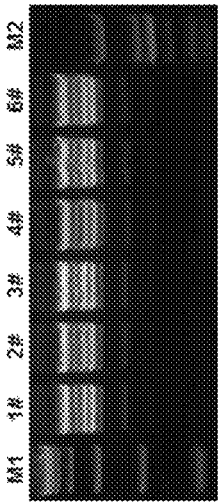
Fig. 1B pVAX-delE1(L+R) PCR Analysis
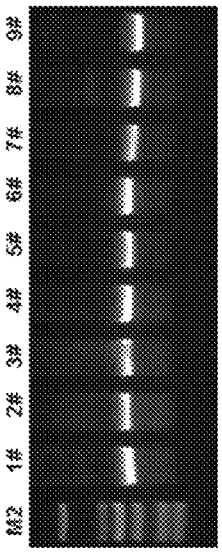
Fig. 1C pAd55-ΔE1ΔE3-kana Endonuclease Digestion Analysis

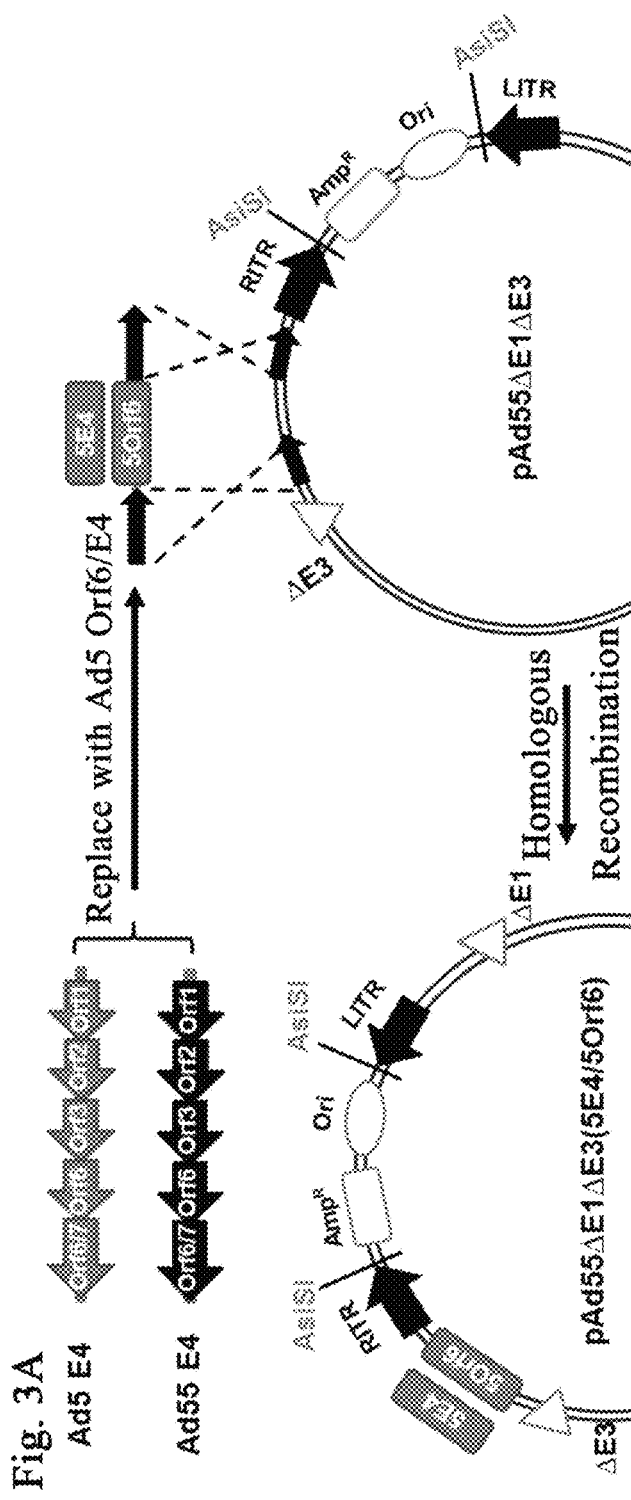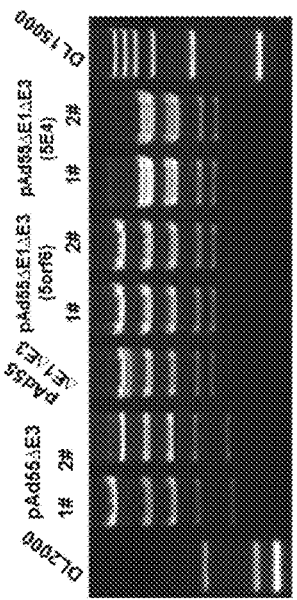
Fig. 3A
Fig. 3B
Fig. 3C

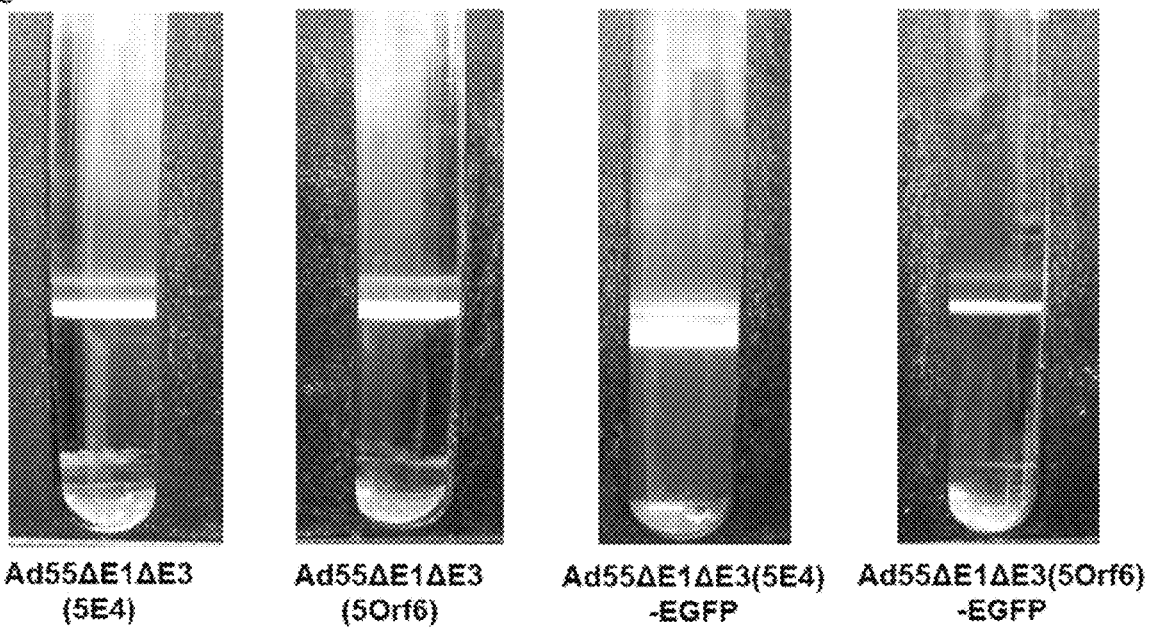

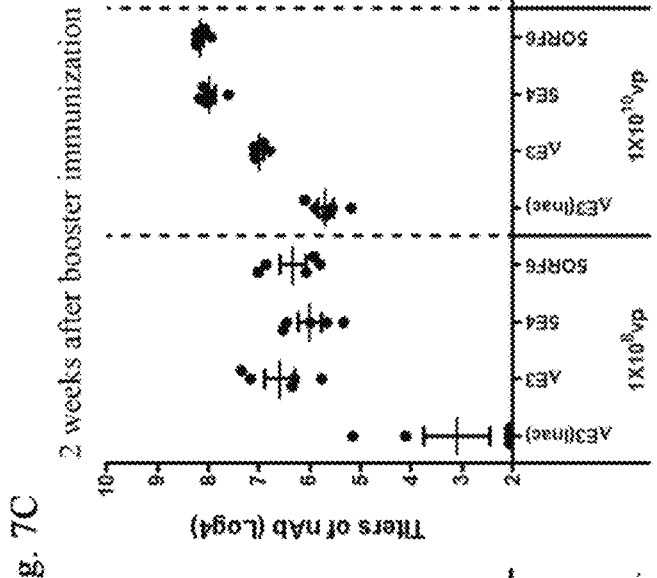
Fig. 7A
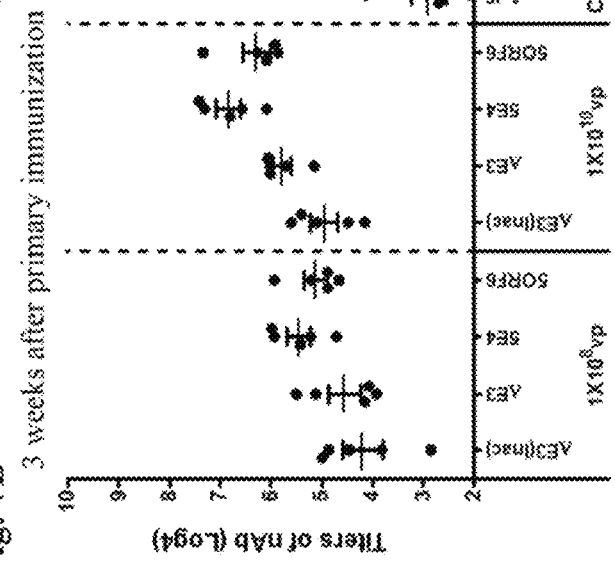
Fig. 7B
Fig. 7C

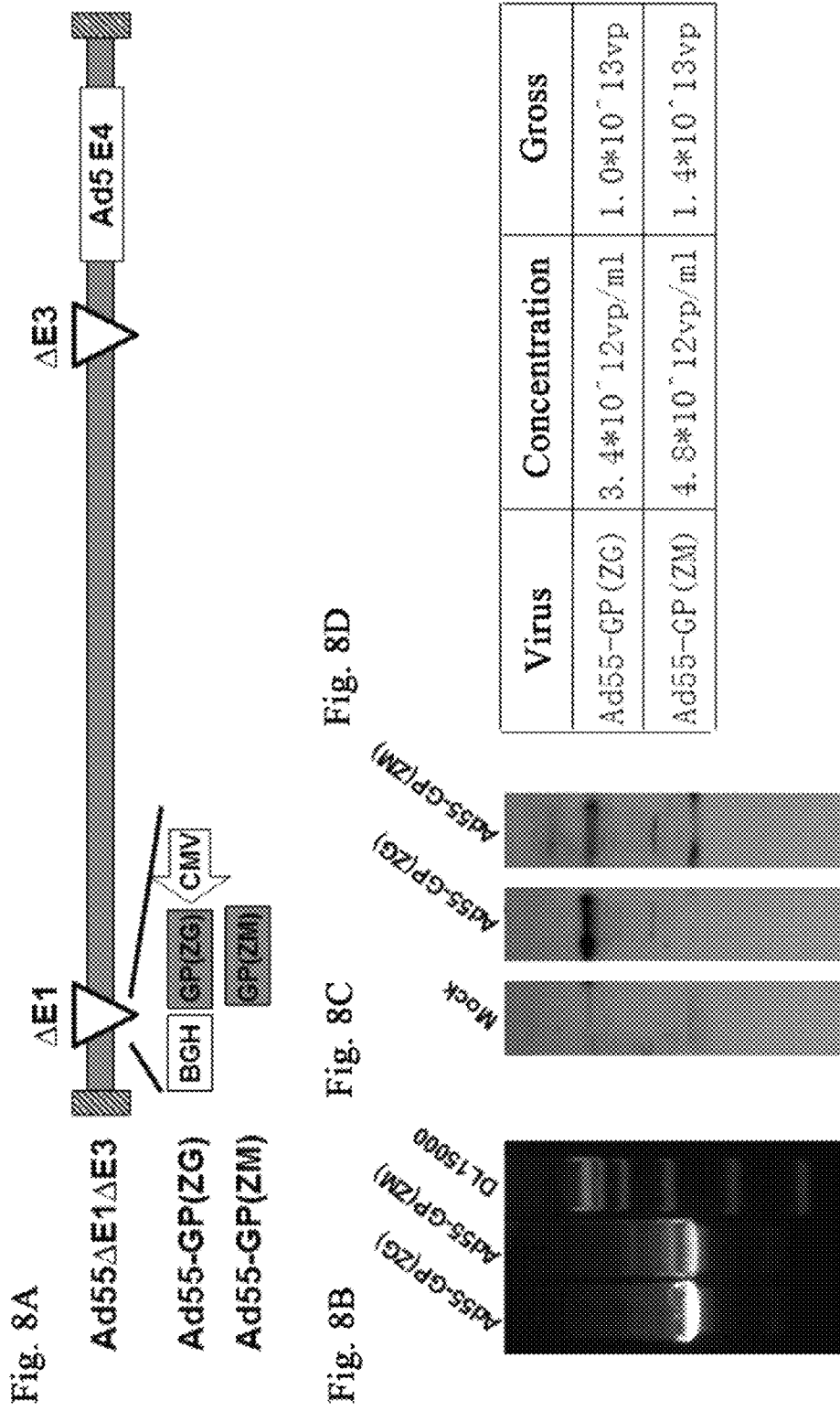

SEQUENCE LISTING

<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
atagaattcg gggtggagtg tttttgcaag                                30

<210> SEQ ID NO 2
<211> LENGTH: 41
<212> TYPE: DNA
<213> ORGANISM: Artificial Sequence
<220> FEATURE:
<223> OTHER INFORMATION: Synthetic

<400> SEQUENCE: 2
tttactagtg tttaaacgta atcgaaacct ccacgtaatg g                   41

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3
atttctagag tttaaacgag accggatcat ttggttattg                     40

<210> SEQ ID NO 4
<211> LENGTH: 31
<212> TYPE: DNA
<213> ORGANISM: Artificial Sequence
<220> FEATURE:
<223> OTHER INFORMATION: Synthetic

<400> SEQUENCE: 4
aaagaattcg ggaaatgcaa atctgtgagg g                              31

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
ataactagtg gggtggagtg tttttgcaag                                30

<210> SEQ ID NO 6
<211> LENGTH: 41
<212> TYPE: DNA
<213> ORGANISM: Artificial Sequence
<220> FEATURE:
<223> OTHER INFORMATION: Synthetic

<400> SEQUENCE: 6
tttgaattcg tttaaacgta atcgaaacct ccacgtaatg g                   41

<210> SEQ ID NO 7
<211> LENGTH: 34
<212> TYPE: DNA
<213> ORGANISM: Artificial Sequence

```
<220> FEATURE:
<223> OTHER INFORMATION: Synthetic

<400> SEQUENCE: 7 atcgttttaaa cgagaccgga tcatttggtt attg                              34

<210> SEQ ID NO 8
<211> LENGTH: 31
<212> TYPE: DNA
<213> ORGANISM: Artificial Sequence
<220> FEATURE:
<223> OTHER INFORMATION: Synthetic

<400> SEQUENCE: 8
atctctagag ggaaatgcaa atctgtgagg g                                  31

<210> SEQ ID NO 9
<211> LENGTH: 34
<212> TYPE: DNA
<213> ORGANISM: Artificial Sequence
<220> FEATURE:
<223> OTHER INFORMATION: Synthetic

<400> SEQUENCE: 9
gatcacgcgt ggactaagag acctgctacc catg                              34

<210> SEQ ID NO 10
<211> LENGTH: 42
<212> TYPE: DNA
<213> ORGANISM: Artificial Sequence
<220> FEATURE:
<223> OTHER INFORMATION: Synthetic

<400> SEQUENCE: 10
tgtagatctg tttaaacctt tagccccatt acgtcagttt ag                     42

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11
ttacgctctt cctagccgtg atccagactc cgg                               33

<210> SEQ ID NO 12
<211> LENGTH: 39
<212> TYPE: DNA
<213> ORGANISM: Artificial Sequence
<220> FEATURE:
<223> OTHER INFORMATION: Synthetic

<400> SEQUENCE: 12
agctgctctt cccattctcg tattttgtat agcaaaacg                         39

<210> SEQ ID NO 13
<211> LENGTH: 37
<212> TYPE: DNA
<213> ORGANISM: Artificial Sequence
<220> FEATURE:
<223> OTHER INFORMATION: Synthetic

<400> SEQUENCE: 13
aatagctctt ccctacatgg gggtagagtc ataatcg                           37
```

<210> SEQ ID NO 14
<211> LENGTH: 32
<212> TYPE: DNA
<213> ORGANISM: Artificial Sequence
<220> FEATURE:
<223> OTHER INFORMATION: Synthetic

<400> SEQUENCE: 14
actagctctt ccatgactac gtccggcgtt cc                                32

<210> SEQ ID NO 15
<211> LENGTH: 37
<212> TYPE: DNA
<213> ORGANISM: Artificial Sequence
<220> FEATURE:
<223> OTHER INFORMATION: Synthetic

<400> SEQUENCE: 15
atagctcttc ccattgttag ttttgaatga gtctgca                           37

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
atatgctctt ccatgcagaa acccgcagac atg                               33

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
aatggtaccg gggtggagtg tttttgcaag                                   30

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
atcgtaatcg aaacctccac gtaatgg                                      27

<210> SEQ ID NO 19
<211> LENGTH: 32
<212> TYPE: DNA
<213> ORGANISM: Artificial Sequence
<220> FEATURE:
<223> OTHER INFORMATION: Synthetic

<400> SEQUENCE: 19
aacactagtg agaccggatc atttggttat tg                                32

<210> SEQ ID NO 20
<211> LENGTH: 37
<212> TYPE: DNA
<213> ORGANISM: Artificial Sequence
<220> FEATURE:
<223> OTHER INFORMATION: Synthetic

```
<400> SEQUENCE: 20
ttaacgcgtg tatacgggaa atgcaaatct gtgaggg                    37

<210> SEQ ID NO 21
<211> LENGTH: 32
<212> TYPE: DNA
<213> ORGANISM: Artificial Sequence
<220> FEATURE:
<223> OTHER INFORMATION: Synthetic

<400> SEQUENCE: 21
agatatacgc gttgacattg attattgact ag                         32

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
gctggttctt tccgcctcag aag                                   23
```

HUMAN TYPE 55 REPLICATION DEFECTIVE ADENOVIRUS VECTOR, METHOD FOR PREPARING SAME AND USES THEREOF

CROSS-REFERENCE TO RELATED APPLICATIONS

This present application is a Continuation Application of PCT application No. PCT/CN2015/095730 filed on Nov. 27, 2015, which claims the benefit of Chinese Patent Application No. 201510179459.7 filed on Apr. 15, 2015, the contents of which are hereby incorporated by reference.

REFERENCE TO SEQUENCE LISTING

The Sequence Listing is submitted as an ASCII formatted text filed via EFS-Web, with a file name of "Sequence Listing.TXT", a creation date of Oct. 16, 2017, and a size of 4,310 bytes. The sequence listing filed via EFS-Web is part of the specification and is incorporated in its entirety by reference herein.

FIELD OF THE INVENTION

The present invention relates to biotechnical field, and more particularly to a human type 55 replication defective adenovirus vector, method for preparing the same and uses thereof.

BACKGROUND OF THE INVENTION

Adenovirus (Ad) is a double-stranded DNA virus with a genome length of about 35-40 kb. It is known that human adenovirus is classified into 7 species (A-G) including more than 60 serotypes. Adenovirus type 3, 4, 7 and 14, belonging to species B, can cause acute respiratory diseases and even fatal pneumonia. In recent years, the emergence of type 55 adenovirus (hereinafter referred to as Ad55) which is a recombinant virus of type 11 and 14 adenoviruses, has led to a series of outbreaks of community-acquired pneumonia. Death cases were sporadically reported in these epidemics. Clinically, supportive treatment is the only strategy for Ad55 infection. There are still no anti-viral drugs nor prophylactic vaccines. Therefore, development of anti-Ad55 vaccines and drugs is essential for the control of Ad55 infection in general populations, especially among military recruits, young students and the like.

At present, the only adenovirus vaccine is used in US troops. This vaccine is enteric-coated capsules comprised of wild type Ad4 and Ad7 which are passaged and propagated on diploid human fetal kidney fibroblasts, and then frozen, dehydrated, and coated with cellulose lactose. The utilization of this vaccine effectively decreased the outbreaks of adenovirus epidemic in US troops. However, the used adenovirus vaccine is still of significant drawbacks. This vaccine is mainly used to prevent Ad4 and Ad7 infection, and has no exact preventive effects on Ad14 and Ad55 which are highly pathogenic. On the other hand, this vaccine is comprised of wild-type adenovirus, which may bring safety concerns because residual live viruses discharged from the intestinal tract can easily pollute the water and thus resulting in the spread of the viruses. This vaccine, therefore, cannot be applied to general population. Replication defective adenovirus vaccine with high safety and protective capacity against Ad55 is urgently needed.

Previous studies have shown that E1 gene is essential for the replication of adenovirus, whereas E3 gene antagonizes host immune responses. Adenovirus with E1 and E3 genes deleted lose the ability to replicate in immune-competent individuals and exhibit an attenuated phenotype, whereas the major surface antigens such as Hexon and Fibre are not affected. Therefore, the use of replication defective adenovirus as a vaccine can effectively enhance its safety and expand its applicable range. Replication defective adenovirus can be propagated in complementary cell lines, such as 293 and PerC6 cells, which steadily express the E1 gene of Ad5. However, for many adenoviruses, especially those from species B, deletion of E1 and E3 genes renders them difficult to propagate in these cell lines, mainly because Ad5 E1B 55K cannot interact with E4 Orf6 from species B adenovirus, and thereby cannot effectively inhibit host mRNA transportation out of the nucleus and enhance the expression of viral late proteins.

Replication defective Ad55 can also be widely used as gene vector in gene therapy, as well as vaccines and other fields. Adenovirus vector has a number of advantages such as good safety, effectiveness of gene transduction and convenience of large-scale production. Due to these advantages, adenovirus vector has been used in hundreds of clinical trials around the world, ranking among the most widely used vectors (24.8%). Most studies use Ad5 or Ad2 as vector. However, the pre-existing anti-Ad immune response elicited by previous adenovirus infection limits the use of traditional adenovirus vector. Studies have shown that pre-existing Ad2 and Ad5 neutralizing antibodies are of high seropositive rate in developing countries and regions such as Africa, South America and China. In some populations the seropositive rate is even more than 90%. These neutralizing antibodies inhibit the entry of adenovirus vectors into body cells, making it difficult to perform immunological or therapeutic functions. To overcome the pre-existing anti-Ad immune response, researchers have developed a series of techniques, including: 1) using immunosuppressive agents to inhibit the anti-Ad immune response such as cyclosporine, cyclophosphamide, FK506, etc.; 2) modifying or reconstructing surface proteins of adenovirus vector in order to bypass pre-existing neutralizing antibodies; 3) infecting PBMC by adenovirus in vitro, then performing autologous transfusion (an AVIP techniques which we have previously developed), and so on. However, these techniques either have severe side effects (such as immunosuppressive agents) or can only be used for once because of the immune response triggered against a new vector after the application.

SUMMARY OF THE INVENTION

The technical problem to be solved by the present invention is to provide a human type 55 replication defective adenovirus vector in order to overcome the above-mentioned problems of the prior art.

The above technical problems will be resolved by the following technical solutions:

A human type 55 replication defective adenovirus vector is prepared by the following method: knocking out E1 and E3 genes of Ad55 and then substituting the open reading frame (Orf) 6 or Orf 2, 3, 4, 6, and 6/7 of E4 gene in Ad55 genome with corresponding reading frames of Ad5 genome.

Preferably, the human type 55 replication defective adenovirus vector also integrates exogenous gene expression cassette in the E1 gene region.

A method for preparing a human type 55 replication defective adenovirus vector comprises the following steps:

S1. Amplifying homologous recombination arms of the Ad55 E1 gene region by PCR and ligating the arms backward into a vector with kanamycin resistance (Kana$^R$) gene, linearizing the vector, obtaining a genomic plasmid pAd55ΔE1ΔE3-Kana through homologous recombination of the linearized vector with pAd55ΔE3, which is linearized by partial digestion;

S2. Amplifying homologous recombination arms of the Ad55 E1 gene region by PCR, ligating the arms forward into a vector with Kana$^R$ gene, linearizing the vector, obtaining a genomic plasmid pAd55ΔE1ΔE3 through homologous recombination of the linearized vector with the linearized pAd55ΔE1ΔE3-Kana;

S3. Amplifying the Ad5 E4 Orf2-6 and Ad55 E4 genes by PCR, substituting a corresponding region of the Ad55 E4 gene with Ad5 E4 Orf2-6 to obtain p55E4(5E4), linearizing the p55E4(5E4), obtaining a genomic plasmid pAd55ΔE1ΔE3(5E4) through homologous recombination of the linearized p55E4(5E4) with the linearized pAd55ΔE1ΔE3;

S4. Amplifying Ad5 E4 Orf6 by PCR, substituting the corresponding region of the Ad55 E4 gene mentioned in S3 with the amplified Ad5 E4 Orf6 to obtain p55E4(5Orf6), linearizing the p55E4(5Orf6), obtaining a genomic plasmid pAd55ΔE1ΔE3(5Orf6) through homologous recombination of the linearized p55E4(5Orf6) with the linearized pAd55ΔE1ΔE3.

Preferably, a specific process of step S1 comprises of:

Amplifying homologous recombination arms L-delE1 and R-delE1 of the E1 gene by PCR using the Ad55 genome as a template, ligating the arms into a pVax vector after digestion to obtain pVax-delE1(L+R), linearizing the pVax-delE1(L+R), obtaining the genomic plasmid pAd55ΔE1ΔE3-Kana with the E1 and E3 genes knocked out and a unique restriction site PmeI introduced through homologous recombination of the linearized pVax-delE1(L+R) with pAd55ΔE3 linearized by partial digestion and ampicillin and kanamycin dual-resistance screening.

Most preferably, in an embodiment of the present invention, a specific process of step S1 comprises of:

Amplifying upstream and downstream recombination arms L-delE1 and R-delE1 of the E1 gene by PCR using Ad55 genome as the template, digesting the L-delE1 with SpeI and EcoRI, ligating the digested L-delE1 into the pVax vector digested with the same endonucleases to obtain pVax-L-delE1; digesting the R-delE1 with EcoRI and XbaI, ligating the digested R-delE1 into pVax-L-delE1 digested with the same endonucleases to obtain the shuttle plasmid pVax-delE1(L+R) with the E1 gene knocked out;

Linearizing pVax-delE1(L+R) with EcoRI and linearizing pAd55ΔE3 by partial digestion with PacI, obtaining the genomic plasmid pAd55ΔE1ΔE3-Kana through homologous recombination of the two linearized fragments and dual-resistance screening.

Preferably, a specific process of step S2 comprises of:

Amplifying homologous recombination aims L-delK(E1) and R-delK(E1) of the E1 gene by PCR using the Ad55 genome as a template, ligating the arms into a pVax vector after digestion to obtain pVax-delK(E1), linearizing the pVax-delK(E1), obtaining the genomic plasmid pAd55ΔE1ΔE3 with the E1, E3 and Kana$^R$ genes knocked out and a unique restriction site PmeI introduced through homologous recombination of the linearized pVax-delK(E1) with the linearized pAd55ΔE1ΔE3-Knana.

Most preferably, in an embodiment of the present invention, a specific process of step S2 comprises of:

Amplifying upstream and downstream recombination arms L-delK and R-delK of the E1 gene by PCR using the Ad55 genome as the template, digesting the L-delK with SpeI and EcoRI, ligateing the digested L-delK into the pVax vector digested with the same endonucleases to obtain pVax-L-delK(E1); digesting the R-delK with EcoRI and XbaI, ligating the digested R-delK into pVax-L-delK(E1) digested with the same endonucleases to obtain the shuttle plasmid pVax-delK (E1) with the kana$^R$ gene knocked out;

Linearizing pVax-delK(E1) by digestion with SpeI and EcoRI and linearizing pAd55ΔE3-Kana with PmeI, obtaining the genomic plasmid pAd55ΔE1ΔE3 with the kana$^R$ gene knocked out and unique restriction site PmeI introduced in the original E1 gene region through homologous recombination of the two linearized fragments.

Preferably, a specific process of step S3 comprises of:

Amplifying Ad5 E4 Orf2-6 and Ad55 E4 by PCR using Ad5 genome and Ad55 genome as templates respectively, ligating the Ad55 E4 into a T vector to obtain p55E4, further removing Ad55 E4 Orf2-6 by PCR using p55E4 as a template, then ligating the PCR product with the Ad5 E4 Orf2-6 to obtain p55E4(5E4), linearizing the p55E4(5E4), and obtaining pAd55ΔE1ΔE3(5E4) through homologous recombination of the linearized p55E4(5E4) with the linearized pAd55ΔE1ΔE3.

Most preferably, in an embodiment of the present invention, a specific process of step S3 comprises of:

Amplifying Ad5 E4 Orf2-6 gene and Ad55 E4 gene by PCR using Ad5 genome and Ad55 genome as templates respectively, ligating each into the T vectors to obtain p5Orf2-6 and p55E4 respectively; removing E4 Orf2-6 of Ad55 by PCR using p55E4 as the template and introducing the restriction site SapI, digesting the two vectors with SapI and then ligating each other to obtain p55E4(5E4);

Digesting p55E4(5E4) with PmeI and MluI and digesting pAd55ΔE1ΔE3 with PsiI, obtaining the genomic plasmid pAd55ΔE1ΔE3(5E4) of which Ad55 E4 Orf2-6 is substituted with Ad5 E4 Orf2-6 through homologous recombination.

Preferably, a specific process of step S4 comprises of:

Amplifying Ad5 E4 Orf6 by PCR using Ad5 genome as a template, removing Ad55 E4 Orf6 from p55E4 by PCR, ligating the two PCR products to obtain p55E4(5Orf6), linearizing the p55E4(5Orf6), obtaining pAd55ΔE1ΔE3 (5Orf6) through homologous recombination of the linearized p55E4(5Orf6) with the linearized pAd55ΔE1ΔE3.

Most preferably, in an embodiment of the present invention, a specific process of step S4 comprises of:

Amplifying Ad5 E4 Orf6 using p5Orf2-6 and p55E4 as templates and introducing a restriction site SapI by PCR, removing Ad55 E4 Orf6 from p55E4, digesting the two PCR products with SapI and then ligating each other to obtain p55E4(5Orf6);

Digesting p55E4(5Orf6) with PmeI and MluI and digesting pAd55ΔE1ΔE3 with PsiI, obtaining the genomic plasmid pAd55ΔE1ΔE3(5Orf6) of which Ad55 E4 Orf6 is substituted with Ad5 E4 Orf6 through homologous recombination.

A method for preparing a human type 55 replication defective adenovirus vector also comprises the following steps:

S5 Amplifying homologous recombination ail is SE1L and SE1R of the E1 gene by PCR using the Ad55 genome as a template, digesting the aims and ligating the digested products into a pVax vector to obtain pSE1LR; amplifying an exogenous gene expression cassette CMV-EGFP-BGH by PCR using pGA1-EGFP as a template, digesting the pSE1LR and CMV-EGFP-BGH, ligating the two digested products to obtain pGK551-EGFP, linearizing the pGK551-EGFP, obtaining pAd55ΔE1ΔE3(5E4)-EGFP and pAd55ΔE1ΔE3(5Orf6)-EGFP through homologous recombination of the linearized pGK551-EGFP with the linearized pAd55ΔE1ΔE3 (5 E4) and pAd55ΔE1ΔE3(5Orf6) (mentioned in S3 step and S4 step) respectively, then transfecting the pAd55ΔE1ΔE3(5E4)-EGFP and pAd55ΔE1ΔE3 (5Orf6)-EGFP into 293 cells after linearization, and obtaining human type 55 replication defective adenovirus vectors by centrifugal purification afterwards.

Preferably, a specific process of step S5 comprises of:

S5(1). Using the pVax, Ad55 genome and pGA1-EGFP as PCR templates respectively to obtain a Vax backbone, upstream and downstream homologous recombination arms SE1L and SE1R of the E1 gene region, the exogenous gene expression cassette CMV-EGFP-BGH; digesting the Vax backbone, SE1L and SE1R, then ligating each to obtain pSE1LR; digesting the CMV-EGFP-BGH and pSE1LR, then ligating each to obtain the shuttle plasmid pGK551-EGFP;

S5(2). Obtaining pAd55ΔE1ΔE3(5E4)-EGFP and pAd55ΔE1ΔE3(5Orf6)-EGFP through homologous recombination of the linearized pGK551-EGFP with the linearized pAd55ΔE1ΔE3(5E4) and pAd55ΔE1ΔE3(5Orf6) respectively;

S5(3). Linearizing pAd55ΔE1ΔE3 (5E4), pAd55ΔE1ΔE3 (5Orf6), pAd55ΔE1ΔE3(5E4)-EGFP and pAd55ΔE1ΔE3 (5Orf6)-EGFP with AsiSI, transfecting 293 cells with the linearized plasmids, obtaining purified human type 55 replication defective adenovirus vectors Ad55ΔE1ΔE3(5E4), Ad55ΔE1ΔE3(5Orf6), Ad55ΔE1ΔE3 (5E4)-EGFP and Ad55ΔE1ΔE3(5Orf6)-EGFP after amplification and density gradient centrifugation.

Most preferably, in an embodiment, a specific process of step S5 comprises of:

S5(1). Using the pVax and Ad55 genome as PCR templates respectively to obtain the Vax backbone, upstream and downstream homologous recombination aims SE1L and SE1R of the E1 gene region, digesting the Vax backbone with SpeI and SE1L with XbaI followed by phosphorylation, ligating the two fragments to obtain pSE1L; digesting pSE1L and SE1R with SpeI and EcoRV and ligating each to obtain pSE1R; using pGA1-EGFP as a template to obtain CMV-EGFP-BGH by PCR, digesting CMV-EGFP-BGH and pSE1LR with SpeI and EcoRV and ligating each to obtain the desired shuttle plasmid pGK551-EGFP with exogenous gene expression cassette;

S5(2). Digesting pGK551-EGFP with BstZ17I and SgrAI, and pAd55ΔE1ΔE3(5E4) and pAd55ΔE1ΔE3(5Orf6) with PmeI, obtaining pAd55ΔE1ΔE3(5E4)-EGFP and pAd55ΔE1ΔE3(5Orf6)-EGFP through homologous recombination of the digested pGK551-EGFP with the digested pAd55ΔE1ΔE3 (5 E4) and pAd55ΔE1ΔE3(5Orf6) respectively;

S5(3). Linearizing pAd55ΔE1ΔE3 (5E4), pAd55ΔE1ΔE3 (5Orf6), pAd55ΔE1ΔE3(5E4)-EGFP and pAd55ΔE1ΔE3 (5Orf6)-EGFP with AsiSI, transfecting 293 cells for rescue and amplification of the linearized plasmids, obtaining purified human type 55 replication defective adenovirus vectors Ad55ΔE1ΔE3 (5 E4), Ad55ΔE1ΔE3 (5 Orf6), Ad55ΔE1ΔE3 (5E4)-EGFP and Ad55ΔE1ΔE3(5Orf6)-EGFP by density gradient centrifugation.

Use of the human type 55 replication defective adenovirus vector for preparing vaccines.

Use of the human type 55 replication defective adenovirus vector for preparing neutralizing antibodies.

Use of the human type 55 replication defective adenovirus vector in biological reporter-tracer systems.

Use of the human type 55 replication defective adenovirus vector for preparing vaccines against human Ad55.

Uses of the human type 55 replication defective adenovirus vector for preparing drugs against human Ad55.

Beneficial effects: (1) the vectors of the present invention can be produced in helper cell lines such as 293 and PerC6 in large scale, can be purified by density gradient centrifugation, and have an attenuated phenotype for the lack of replication capacity in normal human cells; (2) the recombinant vectors can also express exogenous genes in target cells efficiently; (3) the recombinant vectors of the present invention can be used as vaccines or gene therapy vectors, and can also be used in research and development of drugs and neutralizing antibodies, as well as in reporter-tracer systems, etc.

DESCRIPTION OF THE DRAWINGS

FIG. 1A shows the principle of knocking out E1 gene from pAd55ΔE3 using dual-resistance screening technology. FIG. 1B shows the detection of R-delE1 fragments in pVAX-delE1(L+R) by PCR assay (M2: DNA Ladder 2000; 1# to 8#: different pVAX-delE1(L+R) clones; 9#: positive control). FIG. 1C shows the endonuclease digestion analysis of pAd55ΔE1ΔE3-Kana with HindIII and BamHI (M1: DNA Ladder 15000; 1# to 6#: different pAd55ΔE1ΔE3-Kana clones; M2: DNA Ladder 2000).

FIG. 3A shows the principle of replacement of E4 Orf6 and E4 Orf2-6 of pAd55ΔE1ΔE3 with Ad5 E4 Orf6 and Ad5 E4 Orf2-6 respectively. FIG. 3B shows the endonuclease digestion analysis of p55E4(5Orf6) with EcoRV and MluI, and the endonuclease digestion analysis of p55E4(5E4) with EcoRV and HindIII (DL15000: DNA Ladder 15000; 1# to 6#: different p55E4(5Orf6) clones and p55E4(5E4) clones). FIG. 3C shows the endonuclease digestion analysis of the pAd55ΔE1ΔE3(5Orf6) and pAd55ΔE1ΔE3(5E4) with HindIII (DL2000: DNA Ladder 2000; pAd55ΔE3 and pAd55ΔE1ΔE3 are used as controls; 1#, 2#: different pAd55ΔE1ΔE3(5Orf6) clones and pAd55ΔE1ΔE3(5E4) clones; DL15000: DNA Ladder 15000.

FIG. 5A shows the purification of Ad55ΔE1ΔE3(5E4), Ad55ΔE1ΔE3 (5 Orf6), Ad55ΔE1ΔE3(5E4)-EGFP, and Ad55ΔE1ΔE3(5Orf6)-EGFP by cesium chloride density gradient centrifugation. FIG. 5B shows the results of titration of these viruses.

FIG. 7A shows the immunization schedules for assessing the immunogenicity of replication defective Ad55 vectors. FIG. 7B shows the neutralizing antibody responses elicited by inactive Ad55, replication competent Ad55 and replication defective Ad55 in mice at 3 weeks after the first immunization. FIG. 7C shows the neutralizing antibody responses elicited by inactive Ad55, replication competent Ad55 and replication defective Ad55 in mice at 2 weeks after the second immunization.

FIG. 8A shows the genomic structure of replication defective Ad55 vectors harboring GP gene of Ebola virus. FIG. 8B shows the detection of Ad55-GP(ZG) and Ad55-GP(ZM) by PCR assay. FIG. 8C shows the Western-blot analysis of GP expression in 293 cells infected with Ad55-GP(ZG) and Ad55-GP(ZM). FIG. 8D shows the results of production and purification of replication defective Ad55 expressing GP derived from ebola virus.

DETAILED DESCRIPTION OF THE INVENTION

The present invention discloses a method for preparing a human type 55 replication defective adenovirus vector. The preparation method and construction idea of the adenovirus vector of the invention can be applied to developing vaccines against adenovirus and other pathogenic viruses, screening anti-adenovirus drugs and neutralizing antibodies, and developing biological reporter-tracer systems.

The term "human type 55 adenovirus" in the present invention refers to type 55 adenovirus known to one skilled in the art, and the Ad55 genome used in the embodiments is also derived from these known human type 55 adenoviruses. The human type 55 replication defective adenovirus vector of the present invention is not limited to the particular clinical isolates employed in the embodiments.

The term "exogenous sequence" of the present invention refers to any DNA sequence not derived from Ad55. One skilled in the art should recognize that the exogenous sequence may be an exogenous gene expression cassette, or a shRNA or miRNA expression cassette.

In the following embodiments, the exogenous gene expression cassette may comprise a eukaryotic promoter, an exogenous gene coding sequence and a transcription terminator, as understood by one skilled in the art. The exogenous gene coding sequence may be, but is not limited to, a coding sequence of green fluorescent protein, other viral antigens, or shRNA etc.

In order to provide a clearer understanding of the technical solution of the present invention, the following embodiments are given in detail with reference to drawings. It is to be understood that the embodiments are merely illustration of the invention and are not intended to limit the scope of the invention. Experimental methods not specified in the following embodiments are generally carried out according to conventional conditions, such as those described in Molecular Cloning: Laboratory Manual (Sambrook, et al, 1989, New York, Cold Spring Harbor Laboratory Press), or suggested by the manufacturers. Chemical agents used in the embodiments are commercially available.

Unless otherwise defined, all technical and scientific terms used in the present invention have the same meaning as commonly understood by one skilled in the art. The terminology used in the specification of the present invention is for the purpose of describing particular embodiments only and is not intended to limit the invention.

Example 1

Knockout of E1 Gene and Construction of Plasmid pAd55ΔE1ΔE3-Kana

1. Construction of Shuttle Plasmid pVax-delE1(L+R) with the E1 Gene Knocked Out

The Ad55 genome was used as the PCR template to amplify and obtain the recombinant arms L-delE1 and R-delE1.

L-delE1 primer sequence:

```
L-delE1 F,
                                        (SEQ ID NO. 1)
ATAGAATTCGGGGTGGAGTGTTTTTGCAAG;

L-delE1 R,
                                        (SEQ ID NO. 2)
TTTACTAGTGTTTAAACGTAATCGAAACCTC
CACGTAATGG.
```

PCR program: 95° C., 30 s; 62° C., 30 s; 72° C., 20 s; 25 circles.

R-arm primer sequence:

```
R-delE1 F,
                                        (SEQ ID NO. 3)
ATTTCTAGAGTTTAAACGAGACCGGATCATT
TGGTTATTG;

R-delE1 R,
                                        (SEQ ID NO. 4)
AAAGAATTCGGGAAATGCAAATCTGTGAGGG.
```

PCR program: 95° C., 30 s; 60° C., 30 s; 72° C., 80 s; 25 circles.

The L-delE1 was digested with SpeI and EcoRI and then ligated to pVax vector (Invitrogen) which was digested with the same endonucleases to obtain pVax-L-delE1; R-delE1 was digested with EcoRI and XbaI and then ligated to the pVax-L-delE1 digested with the same endonucleases to obtain shuttle plasmid pVax-delE1(L+R) with the E1 gene knocked out. Detection of R-delE1 in pVAX-delE1(L+R) by PCR assay were shown in FIG. 1B.

2. Construction of Plasmid pAd55ΔE1ΔE3-Kana

The pVax-delE1(L+R) was linearized by EcoRI and the pAd55ΔE3 was linearized by PacI, then the two linearized plasmids were co-transformed into BJ5183 competent cells (Stratagene); after screening with ampicillin and kanamycin, the plasmids were extracted, and further transformed into XL-Blue competent cells (Peking Baihui Biotechnology Co., Ltd.); the plasmids were extracted to obtain plasmid pAd55ΔE1ΔE3-Kana. Restriction maps were constructed using multiple groups of restriction endonuclease. Two PmeI restriction sites were introduced in original E1 gene region of adenovirus genome of the achieved plasmid pAd55ΔE1ΔE3-Kana in order to facilitate subsequent cloning. See a schematic of plasmid construction in FIG. 1A and endonuclease digestion results of pAd55ΔE1ΔE3-Kana with HindIII and BamHI in FIG. 1C.

Example 2

Knockout of Kana$^R$ Gene and Construction of Plasmid pAd55ΔE1ΔE3

1. Construction of shuttle plasmid pVax-delK(L+R) with Kana$^R$-gene knocked out.

The Ad55 genome was used as the PCR template to amplify and obtain recombinant aims L-delK and R-delK.

L-delK primer sequence:

```
L-delK F,
                                    (SEQ ID NO. 5)
ATAACTAGTGGGGTGGAGTGTTTTTGCAAG;

L-delK R,
                                    (SEQ ID NO. 6)
TTTGAATTCGTTTAAACGTAATCGAAACCTCC
ACGTAATGG.
```

PCR program: 95° C., 30 s; 61° C., 30 s; 72° C., 20 s; 25 circles.

R-delK primer sequence:

```
R-delK F,
                                    (SEQ ID NO. 7)
ATCGTTTAAACGAGACCGGATCATTTGGTTATTG;

R-delK R,
                                    (SEQ ID NO. 8)
ATCTCTAGAGGGAAATGCAAATCTGTGAGGG.
```

PCR program: 95° C., 30 s; 60° C., 30 s; 72° C., 80 s; 25 circles.

Figure 2A:
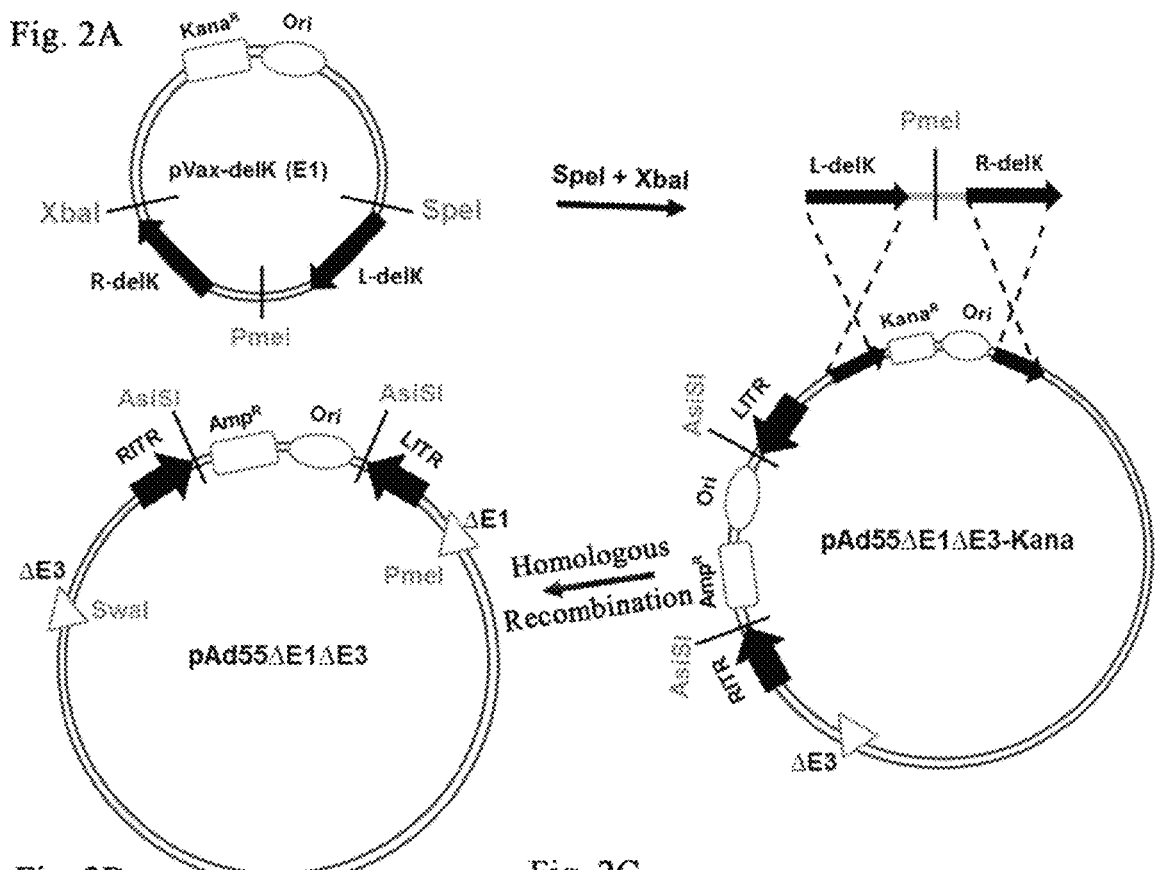
FIG. 2A shows the principle of knocking out kana$^R$ gene from pAd55ΔE1ΔE3-Kana.
Figure 2B:
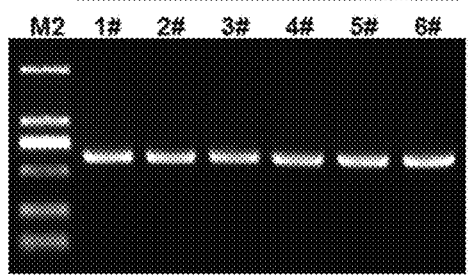
FIG. 2B shows the detection of R-delK fragments in pVAX-delK(E1) by PCR assay (M2: DNA Ladder 2000; 1# to 5#: different pVAX-delK(E1) clones; 6#: positive control).

The L-delK was digested with SpeI and EcoRI and then ligated to pVax vectors (Invitrogen) digested with the same endonucleases to obtain pVax-L-delK; R-delK was digested with EcoRI and XbaI and then ligated to the pVax-L-delE3 digested with the same endonucleases to obtain shuttle plasmid pVax-delK(L+R) of which the Kana$^R$ gene was knocked out. Detection of R-delK in pVAX-delK(E1) by PCR assay were shown in FIG. 2B.

2. Construction of Plasmid pAd55ΔE1ΔE3

Figure 2C:
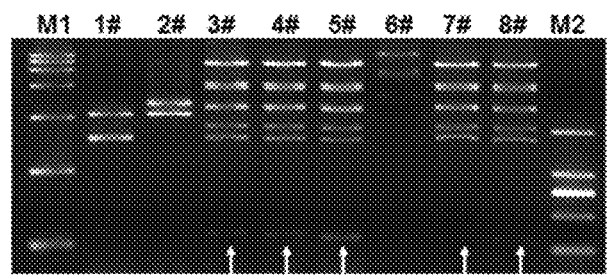
FIG. 2C shows the endonuclease digestion analysis of pAd55ΔE1ΔE3 whereof kana$^R$ gene is knocked out (M1: DNA Ladder 15000; 1# to 8#: different pAd55ΔE1ΔE3-Kana clones, the correct clones are marked by arrows; M2: DNA Ladder 2000).

The pVax-delK(L+R) was linearized with SpeI and XbaI, and the pAd55ΔE1ΔE3-Kana was linearized with PmeI, the two linearized plasmids were then co-transformed into BJ5183 competent cells (Stratagene), then the plasmids were extracted and transformed into XL-Blue competent cells (Peking Baihui Biotechnology Co., Ltd.), then the plasmids were extracted and indentified by restriction analysis. The genomic plasmid pAd55ΔE1ΔE3 was obtained, wherein the Kana$^R$ gene was removed and unique restriction site PmeI was introduced in the E1 region. See a schematic of plasmid construction in FIG. 2A and endonuclease digestion results of pAd55ΔE1ΔE3 in FIG. 2C.

Example 3

Modification of Ad55E4 Gene and Construction of pAd55ΔE1ΔE3(5Orf6) and pAd55ΔE1ΔE3 (5E4)

1. Construction of Shuttle Plasmid with Ad55E4 Gene Modified

1) The Ad55 genome was used as the PCR template to amplify and obtain Ad55E4 gene, and the primers used were as follows:

```
R-delE3 Mlu,
                                    (SEQ ID NO. 9)
GATCACGCGTGGACTAAGAGACCTGCTAC
CCATG;

L-delK R,
                                    (SEQ ID NO. 10)
TGTAGATCTGTTTAAACCTTTAGCCCCATTAC
GTCAGTTTAG.
```

PCR program: 95° C., 30 s; 61° C., 30 s; 72° C., 4 min; 25 circles.

The PCR products were phosphorylated, and were ligated to blunt-ended T vectors (TaKaRa) to obtain p55E4.

2) The p55E4 plasmid was used as the PCR template to amplify and obtain linearized p55E4 with SapI restriction site introduced at the ends and Ad55 E4 Orf6 gene removed.

```
Sap-p55E4 R,
                                    (SEQ ID NO. 11)
TTACGCTCTTCCTAGCCGTGATCCAGACT
CCGG;

Sap-p55E4 orf6 F,
                                    (SEQ ID NO. 12)
AGCTGCTCTTCCCATTCTCGTATTTTGTA
TAGCAAAACG.
```

PCR program: 95° C., 30 s; 63° C., 30 s; 72° C., 5 min; 25 circles.

Ad5 E4 Orf6 gene with SapI site at the ends was obtained by PCR using Ad5 genome as template.

```
Sap-5ORF6 F,
                                    (SEQ ID NO. 13)
AATAGCTCTTCCCTACATGGGGGTAGAGTC
ATAATCG

Sap-5ORF6 R,
                                    (SEQ ID NO. 14)
ACTAGCTCTTCCATGACTACGTCCGGCG
TTCC.
```

PCR program: 95° C., 30 s; 61.5° C., 30 s; 72° C., 45 s; 25 circles.

The linearized p55E4 and Ad5 E4Orf6 were digested with SapI and then ligated with each other to obtain p55E4 (5Orf6).

3) Similarly, the p55E4 plasmid was used as the PCR template to amplify and obtain linearized p55E4 with SapI restriction site and Ad55 E4Orf(2-6) gene knocked out. The primers used were as follows:

```
Sap-p55E4 R,
                                    (SEQ ID NO. 11)
TTACGCTCTTCCTAGCCGTGATCCAGA
CTCCGG;

Sap-p55E4orf2 F,
                                    (SEQ ID NO. 15)
ATAGCTCTTCCCATTGTTAGTTTTGAAT
GAGTCTGCA;
```

PCR program: 95° C., 30 s; 61.5° C., 30 s; 72° C., 4 min; 25 circles.

Ad5 E4Orf(2-6) with SapI site at the ends was obtained by PCR using Ad5 genome as template.

```
Sap-5ORF6 F,
                                 (SEQ ID NO. 13)
AATAGCTCTTCCCTACATGGGGGTAGAG
TCATAATCG;

Sap-5ORF2 R,
                                 (SEQ ID NO. 16)
ATATGCTCTTCCATGCAGAAACCCGCA
GACATG.
```

PCR program: 95° C., 30 s; 61° C., 30 s; 72° C., 2 min; 25 circles.

The linearized p55E4 and Ad5 E4Orf(2-6) fragments were digested with SapI and then ligated with each other to obtain p55E4(5E4).

2. Construction of pAd55ΔE1ΔE3(5Orf6) and pAd55ΔE1ΔE3(5E4).

The p5E4(5Orf6) and p55E4(5E4) were linearized with MluI and PmeI, and the pAd55ΔE1ΔE3 was linearized with PsiI, then the linearized fragments were co-transformed into BJ5183 competent cells to obtain genomic plasmids pAd55ΔE1ΔE3(5Orf6) and pAd55ΔE1ΔE3 (5E4) with E1 and E3 genes knocked out and E4 gene modified through recombination. See a schematic of plasmid construction in FIG. 3A and endonuclease digestion results in FIGS. 3B and 3C. FIG. 3B shows the endonuclease digestion analysis of p55E4(5Orf6) with EcoRV and MluI, and p55E4(5E4) with EcoRV and HindIII. FIG. 3C shows the endonuclease digestion analysis of the pAd55ΔE1ΔE3(5Orf6) and pAd55ΔE1ΔE3(5E4) with HindIII.

Example 4

Construction of Shuttle Plasmid with Exogenous Genes, and Replication Defective Ad55 Genomic Plasmids Such as pAd55ΔE1ΔE3(5Orf6)-EGFP and the Like 1. Construction of Shuttle Plasmid pGK551-EGFP with Exogenous Gene Expression Cassette.

1) Ad55 genome was used as the PCR template to amplify and obtain homologous recombination aims SE1L and SE1R.

SE1L primer sequences:

```
SE1L F,
                                 (SEQ ID NO. 17)
AATGGTACCGGGGTGGAGTGTTTTTGCAAG;

SE1L R,
                                 (SEQ ID NO. 18)
ATCGTAATCGAAACCTCCACGTAATGG.
```

PCR program: 95° C., 30 s; 61° C., 30 s; 72° C., 30 s; 25 circles.

SE1R primer sequences:

```
SE1R F,
                                 (SEQ ID NO. 19)
AACACTAGTGAGACCGGATCATTTGGTTATTG;

SE1R R,
                                 (SEQ ID NO. 20)
TTAACGCGTGTATACGGGAAATGCAAATCTG
TGAGGG.
```

PCR program: 95° C., 30 s; 60° C., 30 s; 72° C., 1 min 30 s; 25 circles.

2) Construction of shuttle plasmids pSE1LR.

pSE3LR and SE1L were digested with KpnI and EcoRV, and then ligated with each other to obtain pSE1L; the pSE1L and SE1R were digested with SpeI and MluI, and then ligated with each other to obtain pSE1LR.

3) Construction of shuttle plasmids pGK551-EGFP and the like with exogenous gene expression cassette.

CMV-EGFP-BGH expression cassette was obtained using pGA1-EGFP as template and the following primer by PCR.

```
CMV,
                                 (SEQ ID NO. 21)
AGATATACGCGTTGACATTGATTATTGACTAG;

BGH,
                                 (SEQ ID NO. 22)
GCTGGTTCTTTCCGCCTCAGAAG.
```

Figure 4A:
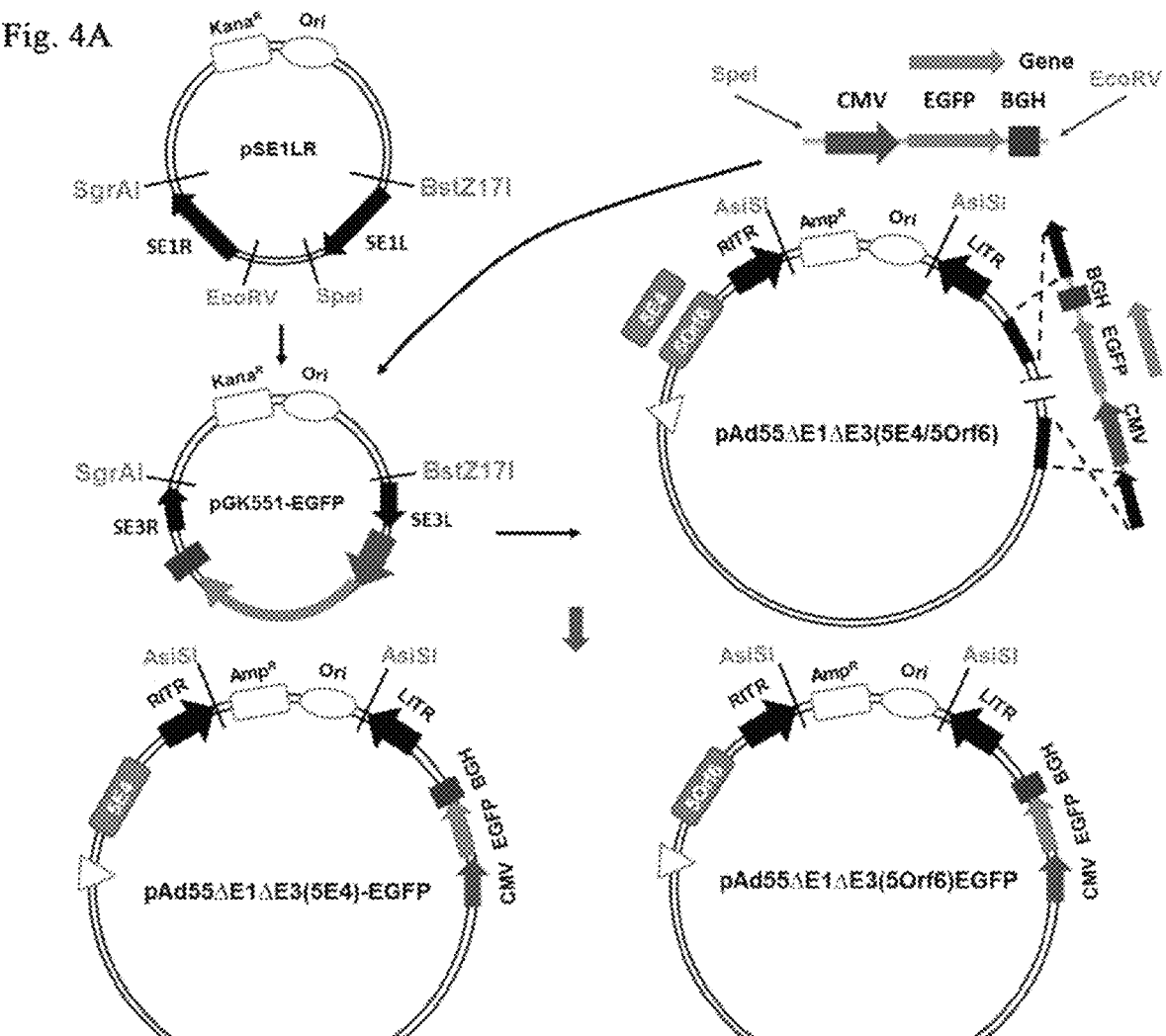
FIG. 4A shows the process of constructing pAd55ΔE1ΔE3(5Orf6)-EGFP and pAd55ΔE1ΔE3(5E4)-EGFP with exogenous gene expression cassettes.
Figure 4B:
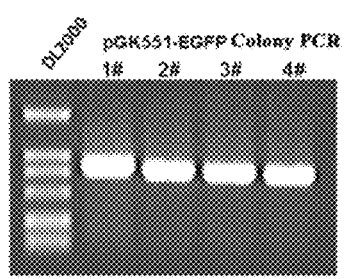
FIG. 4B shows the detection of EGFP in pGK551-EGFP by PCR assay (DL2000: DNA Ladder 2000; 1# to 4#: different pGK551-EGFP clones).

PCR program: 95° C., 30 s; 66° C., 30 s; 72° C., 1 min 45 s; 25 circles.

pSE1LR was digested with SpeI and EcoRV, and CMV-EGFP-BGH was digested with SpeI, then they were ligated with each other to obtain target shuttle plasmid pGK551-EGFP. Detection of EGFP in pGK551-EGFP by PCR assay were shown in FIG. 4B.

Figure 4C:
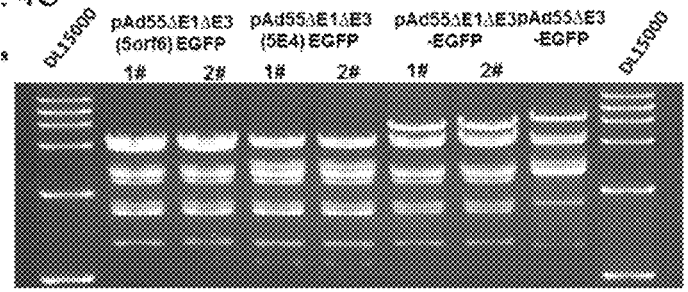
FIG. 4C shows the endonuclease digestion analysis of pAd55ΔE1ΔE3(5Orf6)-EGFP and pAd55ΔE1ΔE3(5E4)-EGFP with HindIII (DL15000: DNA Ladder 15000; pAd55ΔE1ΔE3-EGFP and pAd55ΔE3-EGFP are used as controls).

2. Construction of Genomic Plasmid pAd55ΔE1ΔE3 (5Orf6)-EGFP and the Like.

pG551-EGFP was digested with BstZ17I and SgrAI and recovered by ethanol precipitation; and the pAd55ΔE1ΔE3 (5Orf6) and pAd55ΔE1ΔE3(5E4) were linearized with PmeI and then recovered by ethanol precipitation; then the linearized fragments were co-transformed into BJ5183 to obtain plasmids pAd55ΔE1ΔE3(5Orf6)-EGFP and pAd55ΔE1ΔE3 (5E4)-EGFP with exogenous gene expression cassette through homologous recombination. See a schematic of detailed construction process in FIG. 4A and endonuclease digestion results in FIG. 4C.

Example 5

Rescue and Production of Replication Defective Ad55 Vector

According to a conventional method, the pAd55ΔE1ΔE3 (5Orf6)-EGFP and pAd55ΔE1ΔE3(5E4)-EGFP were linearized with AsiSI and recovered by ethanol precipitation, respectively, and then transfected into 293 cells through cationic liposome. 8 hours after transfection, 2 ml DMEM medium containing 5% fetal bovine serum was added and incubated for 7-10 days, the cell pathogenesis was observed. Subsequently, the cells and culture supernatant were collected, repeatedly freezed and thawed for 3 times in the water bath of 37° C. and liquid nitrogen, and then the cellular debris were removed by centrifugation. The supernatants were added into a 10 cm dish cell cultures. 2-3 days later, the cells and culture supernatant were collected, then the cellular debris were removed by repeated freezing and thawing for 3 times and centrifugation, the supernatants were added into 6-10 15 cm dishes; 2-3 days later, the cells were collected, then the cellular debris were removed by repeated freezing and thawing for 3 times and centrifugation, the supernatants were added into a centrifuge tube of cesium chloride density gradient and centrifuged for 4 hours at 4° C., 35000 rpm; the virus band was separated, desalted and packed; the virus titer was determined by OD260 absorbance under the formula i.e. virus concentration=OD260×dilution factor×36/genome length (kb); the virus solution was stored at −80° C. Purification of the replication defective Ad55 vectors h cesium chloride density gradient centrifugation were shown in FIG. 5A. Values of the virus titer were shown in FIG. 5B.

Example 6

Replication Assay of Replication Defective Ad55 Virus in A549 and 293 Cells

Figure 6:
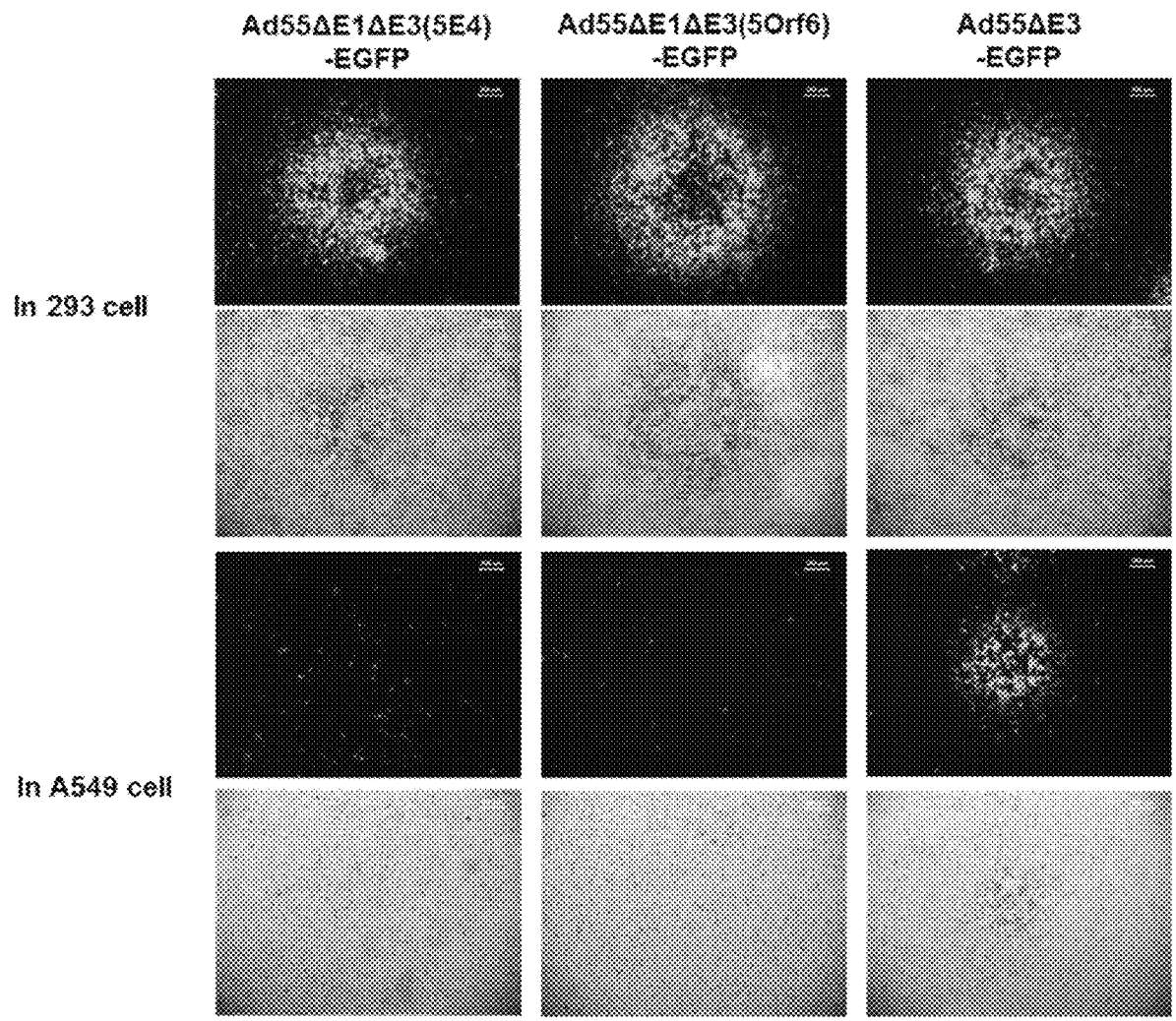
FIG. 6 shows the plaques formed by replication defective Ad55 vectors in 293 and A549 cells. Replication competent Ad55ΔE3-EGFP is used as control. For each type of cells, the upper panel shows the graphs taken under fluorescence field, and the bottom panel shows the graphs taken under bright field.

According to a conventional method, the replication capability of replication defective Ad55 vectors in helper cells 293 and non-helper cell A549 was examined by plaque-forming assay. 90% confluent 293 and A549 cells in 6-well plate were infected with Ad55ΔE1ΔE3(5Orf6)-EGFP, Ad55ΔE1ΔE3(5E4)-EGFP or Ad55ΔE3-EGFP at a dose of $1 \times 10^7$Vp per well. 4 hours after infection, the culture medium was removed and the cells were coated with 1% agarose gel (containing 1% agarose, 5% fetal bovine serum, 1×MEM medium). After 10-12 days' incubation in an incubator at 37° C., the virus plaques were observed with fluorescence microscope and the graphs were taken. The results were shown in FIG. 6. Because Ad55ΔE3-EGFP retained complete E1 gene, it formed typical plaques in both 293 and A549 cells. However, replication defective Ad55ΔE1ΔE3(5Orf6)-EGFP and Ad55ΔE1ΔE3(5E4)-EGFP formed plaques only in 293 cells, but not in A549 cells. These results suggested that replication defective Ad55 vectors efficiently replicated in 293 cells, but could not replicate in non-helper human cells such as A549 cells, and thus exhibiting an attenuated phenotype. Moreover, the results also showed that human type 55 replication defective adenovirus vectors could carry reporter genes into target cells and thus could be used in reporter-tracer systems.

Example 7

Immunogenicity Evaluation of Replication Defective Ad55 Vectors in Mice

Immunogenicity of replication defective Ad55 was evaluated according to the immunization protocol shown in FIG. 7A.

Balb/c mice at 6-8 weeks of age were divided into 9 groups, each group had 5 mice. On day 0, 8 groups of mice were injected intramuscularly with heat-inactivated Ad55ΔE3-EGFP, Ad55ΔE3-EGFP, Ad55ΔE1ΔE3(5Orf6)-EGFP and Ad55ΔE1ΔE3(5E4) at a dose of either $1 \times 10^8$Vp per mice or $1 \times 10^{10}$Vp per mice, respectively. One group of mice was immunized with Ad5ΔE1ΔE3 as control. On day 21, blood samples were collected from orbit and the serum was separated. Meanwhile, the mice were boosted with respective vaccines according to the above protocol. On day 35, the mice were sacrificed and the serum samples were collected. At last, the level of anti-Ad55 neutralizing antibodies in the serums was measured.

According to a conventional method, Ad55E3-SEAP and Ad5-SEAP were used as reporter viruses to detect the neutralizing antibodies against Ad55 and Ad5 in mice serum, respectively. 293 cells were seeded onto 96-well plates. The mice serum was serially diluted with medium free of phenol and serum. The Ad55ΔE3-SEAP or Ad5-SEAP were co-incubated with serum dilutions at a dose of $1 \times 10^7$Vp per sample at 37° C. for an hour, and added to the cell culture plate. After incubation for 24 hours, 50 μl of culture supernatants were transferred to 96-well black plate. The Phospha-Light™ system (Applied Biosystem) was used to detect the ralative light units (shown on the fluorescence illuminometer), and the neutralizing antibody titer was calculated based on the relative light units. The immunized mice could generate Ad55 neutralizing antibody after the primary immunization the neutralization antibody titer in mice was shown in FIG. 7B, and the antibody level increased significantly after the booster immunization, the neutralization antibody titer in mice was shown in FIG. 7C. The titer of the neutralizing antibody induced by inactivated Ad55 was relatively lower than other groups. The titer of the neutralizing antibodies induced by Ad55ΔE1ΔE3(5Orf6)-EGFP and Ad55ΔE1ΔE3(5E4)-EGFP were slightly higher than that induced by Ad55ΔE3-EGFP. These results suggested that replication defective Ad55 vectors were potentially useful in anti-Ad55 vaccine development.

Example 8

Application of Replication Defective Ad55 Vectors in Anti-Ebola Vaccine Development According to the methods described in Examples 4 and 5, the coding sequences for glycoprotein (GP) of Ebola virus (two strains of Zaier subtype, Guinea 2014 and Maynia1976, which were designated as GP (ZG) and GP (ZM) respectively) were codon optimized and cloned into shuttle plasmid pGK551 to obtain pGK551-GP(ZG) and pGK551-GP(ZM). The shuttle plasmids were then linearized with BstZ17I and SgrAI, and recombined with pAd55ΔE1ΔE3(5E4) linearized with PmeI to obtain pAd55-GP(ZG) and pAd55-GP(ZM), respectively. The genomic structure of the replication defective Ad55 vectors harboring GP gene of Ebola virus was illuminated by FIG. 8A. pAd55 GP(ZG) and pAd55-GP(ZM) were further linearized with AsiSI and then transfected into 293 cells. The replication defective Ad55 vectors carrying the Ebola envelope antigen could be rescued and propagated. Ad55-GP(ZG) and Ad55-GP(ZM) were detected by PCR assay (see FIG. 8B), concentration and gross of Ad55-GP(ZG) and Ad55-GP(ZM) produced were determined (see FIG. 8D). The vectors could efficiently express Ebola virus envelope antigen in target cells see FIG. 8C). The results suggested that replication defective Ad55 vectors could be used in studying vaccines against other pathogens.

The examples described above are merely illustrations of several embodiments of the present invention, and the specific and detailed description are not intended to limit the scope of the invention. It should be noted that within the scope of the present invention, various modifications and variations are possible in light of the above teachings for those skilled in the art. Accordingly, the scope of the present invention should be determined by the appended claims.

What is claimed is:

1. A human type 55 replication defective adenovirus vector, comprising type 55 adenovirus (Ad55) genome, wherein:
   E1 and E3 genes of Ad55 are knocked out from the Ad55 genome, and
   open reading frames 2, 3, 4, 5 and 6 of E4 gene in the Ad55 genome are substituted with corresponding open reading frames of type 5 adenovirus (Ad5) genome.

2. The human type 55 replication defective adenovirus vector of claim 1, wherein the vector further comprises an exogenous gene expression cassette which is integrated into a region of Ad55, wherein E1 gene is knocked out from the region.

3. The human type 55 replication defective adenovirus vector of claim 2, wherein the exogenous gene expression cassette is engineered to transcribe genes in a reverse direction relative to the E1 gene of said Ad55 genome.

4. The human type 55 replication defective adenovirus vector of claim 2, wherein the exogenous gene expression cassette comprises nucleotide sequences encoding peptides for inducing immunological responses in human, generating biological reporters and/or tracking molecules.

5. A pharmaceutical composition comprising the human type 55 replication defective adenovirus vector of claim 1 for the preparation of prophylactic or therapeutic reagents against human Ad55 infections.

6. A pharmaceutical composition comprising the human type 55 replication defective adenovirus vector of claim 2 for the preparation of prophylactic or therapeutic reagents against human Ad55 infections.

7. A method for preparing the human type 55 replication defective adenovirus vector of claim 1, comprising the following steps:
   S1. amplifying homologous recombination arms of the E1 gene region of Ad55 by PCR, ligating the arms backward into a vector with Kana$^R$ gene, linearizing the vector, obtaining a genomic plasmid pAd55ΔE1ΔE3-Kana through homologous recombination of the linearized vector with pAd55ΔE3 which is linearized by partial digestion;
   S2. amplifying homologous recombination arms of the E1 gene region of Ad55 by PCR, ligating the arms forward into a vector with Kana$^R$ gene, linearizing the vector, obtaining a genomic plasmid pAd55ΔE1ΔE3 through homologous recombination of the linearized vector with the linearized pAd55ΔE1ΔE3-Kana;
   S3. amplifying Ad5 E4 Orf2-6 and Ad55 E4 genes by PCR, substituting the corresponding E4 gene region of Ad55 with Ad5 E4Orf2-6 to obtain p55E4(5E4), linearizing the p55E4(5E4), obtaining a genomic plasmid pAd55ΔE1ΔE3(5E4) through homologous recombination of the linearized p55E4(5E4) with the linearized pAd55ΔE1ΔE3; and
   S4. amplifying Ad5 E4Orf6 by PCR, substituting the corresponding E4 gene region of Ad55 with the Ad5 E4Orf6 to obtain p55E4(5Orf6), linearizing the p55E4 (5Orf6), obtaining a genomic plasmid pAd55ΔE1ΔE3 (5Orf6) through homologous recombination of the linearized p55E4(5Orf6) with the linearized pAd55ΔE1ΔE3.

8. The method of claim 7, wherein the step S1 comprises amplifying homologous recombination arms L-delE1 and R-delE1 of the E1 gene by PCR using the Ad55 genome as a template, ligating the arms into a pVax vector after digestion to obtain pVax-delE1(L+R), linearizing the pVax-delE1(L+R), obtaining the genomic plasmid pAd55ΔE1ΔE3-Kana with the E1 and E3 genes knocked out and a unique restriction site PmeI introduced through homologous recombination of the linearized pVax-delE1(L+R) with pAd55ΔE1ΔE3 linearized by partial digestion and ampicillin and kanamycin dual-resistance screening.

9. The method of claim 7, wherein the step S2 comprises: amplifying homologous recombination arms L-delK(E1) and R-delK(E1) of the E1 gene by PCR using the Ad55 genome as a template, ligating the arms into a pVax vector after digestion to obtain pVax-delK(E1), linearizing the pVax-delK(E1), obtaining the genomic plasmid pAd55ΔE1ΔE3 with the E1, E3 and kanamycin genes knocked out and a unique restriction site PmeI introduced through homologous recombination of the linearized pVax-delK(E1) with the linearized pAd55ΔE1ΔE3-Kana.

10. The method of claim 7, wherein the step S3 comprises:
amplifying Ad5 E4Orf2-6 and Ad55 E4 by PCR using the Ad5 and Ad55 genomes as templates respectively, ligating the Ad55 E4 into a T vector to obtain p55E4, further removing Ad55 E4Orf2-6 by PCR using the p55E4 as a template, then ligating the PCR product with the Ad5 E4Orf2-6 to obtain p55E4(5E4), linearizing the p55E4(5E4), and obtaining pAd55ΔE1ΔE3 (5E4) through homologous recombination of the linearized p55E4(5E4) with the linearized pAd55ΔE1ΔE3.

11. The method of claim 7, wherein the step S4 comprises:
amplifying Ad5 E4Orf6 by PCR using the Ad5 genome as a template, removing Ad55 E4Orf6 from p55E4 by PCR, ligating the two PCR products to obtain p55E4 (5Orf6), linearizing the p55E4(5Orf6), obtaining pAd55ΔE1ΔE3 (5Orf6) through homologous recombination of the linearized p55E4(5Orf6) with the linearized pAd55ΔE1ΔE3.

12. A method for preparing the human type 55 replication defective adenovirus vector of claim 2, comprising the following steps:
S1. amplifying homologous recombination arms of the E1 gene region of Ad55 by PCR, ligating the arms backward into a vector with Kana$^R$ gene, linearizing the vector, obtaining the genomic plasmid pAd55ΔE1ΔE3-Kana through homologous recombination of the linearized vector with pAd55ΔE3 which is linearized by partial digestion;
S2. amplifying homologous recombination arms of the E1 gene region of Ad55 by PCR, ligating the arms forward into a vector with Kana$^R$ gene, linearizing the vector, obtaining the genomic plasmid pAd55ΔE1ΔE3 through homologous recombination of the linearized vector with the linearized pAd55ΔE1ΔE3-Kana;
S3. amplifying Ad5 E4 Orf2-6 and Ad55 E4 genes by PCR, substituting the corresponding E4 gene region of Ad55 with Ad5 E4Orf2-6 to obtain p55E4(5E4), linearizing the p55E4(5E4), obtaining a genomic plasmid pAd55ΔE1ΔE3(5E4) through homologous recombination of the linearized p55E4(5E4) with the linearized pAd55ΔE1ΔE3; and
S4. amplifying Ad5 E4Orf6 by PCR, substituting the corresponding E4 gene region of Ad55 with the Ad5 E4Orf6 to obtain p55E4(5Orf6), linearizing the p55E4 (5Orf6), obtaining a genomic plasmid pAd55ΔE1ΔE3 (5Orf6) through homologous recombination of the linearized p55E4(5Orf6) with the linearized pAd55ΔE1ΔE3;
S5. amplifying homologous recombination arms SE1L and SE1R of the E1 gene region by PCR using the Ad55 genome as a template, digesting the arms and ligating the digested products into a pVax vector to obtain pSE1LR; producing an exogenous gene expression cassette CMV-EGFP-BGH by PCR using pGA1-EGFP as a template, digesting pSE1LR and CMV-EGFP-BGH, ligating the two digested products to obtain pGK551-EGFP, linearizing pGK551-EGFP, obtaining pAd55ΔE1ΔE3(5E4)-EGFP and pAd55ΔE1ΔE3(5Orf6)-EGFP through homologous recombination of the linearized pGK551-EGFP with the linearized pAd55ΔE1ΔE3(5E4) and pAd55ΔE1ΔE3(5Orf6), respectively, then transfecting the pAd55ΔE1ΔE3(5E4)-EGFP and pAd55ΔE1ΔE3 (5Orf6)-EGFP into 293 cells after further linearization, culturing the transfected cells and obtaining human type 55 replication defective adenovirus vectors by centrifugal purification afterwards.

13. The method of claim 12, wherein the step S1 comprises
amplifying homologous recombination arms L-delE1 and R-delE1 of the E1 gene by PCR using the Ad55 genome as a template, ligating the arms into a pVax vector after digestion to obtain pVax-delE1(L+R), linearizing the pVax-delE1(L+R), obtaining the genomic plasmid pAd55ΔE1ΔE3-Kana with the E1 and E3 genes knocked out and a unique restriction site PmeI introduced through homologous recombination of the linearized pVax-delE1(L+R) with pAd55ΔE1ΔE3 linearized by partial digestion and ampicillin and kanamycin dual-resistance screening.

14. The method of claim 12, wherein the step S2 comprises:
amplifying homologous recombination arms L-delK(E1) and R-delK(E1) of the E1 gene region by PCR using the Ad55 genome as a template, ligating the arms into a pVax vector after digestion to obtain pVax-delK(E1), linearizing the pVax-delK(E1), obtaining the genomic plasmid pAd55ΔE1ΔE3 with the E1, E3 and kanamycin genes knocked out and a unique restriction site PmeI introduced through homologous recombination of the linearized pVax-delK(E1) with the linearized pAd55ΔE1ΔE3-Kana.

15. The method of claim 12, wherein the step S3 comprises:
amplifying Ad5 E4Orf2-6 and Ad55 E4 by PCR using the Ad5 and Ad55 genomes as templates respectively, ligating the Ad55 E4 into a T vector to obtain p55E4, further removing Ad55 E4Orf2-6 by PCR using the p55E4 as a template, then ligating the PCR product with the Ad5 E4Orf2-6 to obtain p55E4(5E4), linearizing the p55E4(5E4), and obtaining pAd55ΔE1ΔE3 (5E4) through homologous recombination of the linearized p55E4(5E4) with the linearized pAd55ΔE1ΔE3.

16. The method of claim 12, wherein the step S4 comprising of:
amplifying Ad5 E4Orf6 by PCR using the Ad5 genome as a template, removing Ad55 E4Orf6 from p55E4 by PCR, ligating the two PCR products to obtain p55E4 (5Orf6), linearizing the p55E4(5Orf6), obtaining pAd55ΔE1ΔE3 (5Orf6) through homologous recombination of the linearized p55E4(5Orf6) with the linearized pAd55ΔE1ΔE3.

* * * * *